United States Patent [19]
Utterberg

[11] Patent Number: 5,562,636
[45] Date of Patent: Oct. 8, 1996

[54] NEEDLE PROTECTOR SHEATH

[76] Inventor: David S. Utterberg, 2033 First Ave. #3, Seattle, Wash. 98121

[21] Appl. No.: 275,880

[22] Filed: Jul. 15, 1994

[51] Int. Cl.⁶ ................................................ A61M 5/00
[52] U.S. Cl. ........................ 604/263; 604/171; 604/177; 604/198
[58] Field of Search .................................. 604/263, 198, 604/192, 177, 110, 174, 162, 197, 163, 171; 128/919

[56] References Cited

U.S. PATENT DOCUMENTS

| | | | |
|---|---|---|---|
| 4,941,881 | 7/1990 | Masters et al. | 604/162 |
| 5,112,311 | 5/1992 | Utterberg et al. | 604/177 |
| 5,120,320 | 6/1992 | Fayngold | 604/177 |
| 5,330,438 | 7/1994 | Gollobin et al. | 604/177 |
| 5,350,368 | 9/1994 | Shields | 604/263 |

*Primary Examiner*—John D. Yasko
*Assistant Examiner*—Ronald K. Stright, Jr.
*Attorney, Agent, or Firm*—Gerstman, Ellis & McMillin, Ltd.

[57] ABSTRACT

A needle protector sheath comprises a body having a top wall, sidewalls and open ends. A slot is formed in each sidewall to slidingly receive a needle wing extending through each of the slots. Typically the slots extend through one end of the protector sheath. The protector sheath also defines an open, bottom aperture extending from end to end of the body, to permit the sheath to be laterally applied to tubing connected to a winged needle and to be advanced to a position where the needle tip is recessed in the sheath and the needle wings extend through the slots.

22 Claims, 3 Drawing Sheets

NEEDLE PROTECTOR SHEATH

BACKGROUND OF THE INVENTION

Utterberg et al. U.S. Pat. No. 5,112,311 discloses a sliding body which is carried on a tubular set such as a fistula set for hemodialysis, having a winged needle at the end. There is a significant need to provide the maximum amount of protection to medical personnel against needle sticks, especially with respect to needles that are used in contact with blood. The sliding member of the cited patent can be brought forward to enclose the needle as the needle is retracted from the patient, so that the needle is immediately secured against accidental needle sticks by the sliding device. The wings of the needle, which are commonly used in conjunction with a variety of intravenous needles, slide within opposed slots of the needle protector of the cited patent, and are locked in place when the needle is fully withdrawn into the sliding body as described.

By this present invention, improvements are provided to the device disclosed in the above-cited patent. Specifically, the device of the prior art is typically placed on a needle set prior to use and the wings engaged in the slots. Even when the sliding sheath is retracted away from the needle as much as possible medical personnel have found its presence to be inconvenient during the process of venipuncture and taping of the needle wings to the skin of the patient.

Also, improvements in functioning are achieved by a modification of the shape of the slots of the sliding sheath or body through which the needle wings penetrate. Particularly, withdrawal of the needle from the patient can be facilitated in an axial movement, reducing the potential for the point to cause a hematoma.

Thus, a significantly improved needle protector is provided, which can be applied to a needle and attached tubing after the needle has been inserted into the vein of a patient. Additionally, other improvements to the prior art are found in this invention.

DESCRIPTION OF THE INVENTION

In accordance with this invention, a needle protector sheath is provided which comprises a body having a top wall, side walls, and at least partially open ends. A slot is formed in at least one of the walls, and preferably in each side wall, to slidingly receive a needle wing extending through each of the slots. The protector sheath defines an open, bottom aperture extending from end to end of the body to permit the sheath to be laterally applied to tubing connected to a winged needle. After such lateral application, the sheath or body can be advanced in sliding manner along the tubing to a position where the needle tip becomes recessed in the sheath, and the needle wing or wings extend through the slot or slots present. Thus the sheath of this invention can be mounted on a needle set after the needle has been placed in a vein or a fistula.

Detents may be provided on the side walls adjacent the bottom aperture to help retain a winged needle, and its connected tubing, within the body of the protector sheath. The bottom aperture is proportioned to permit a needle, needle hub or its connected tubing to be inserted through the bottom aperture for laterally installing the protector sheath onto the tubing of the needle set.

The body of the protector sheath may further define a needle tip retaining wall which is typically formed between the top and side walls adjacent to one end of the body. Such a retaining wall may be positioned substantially parallel to the longitudinal axis of the body to define a closed pocket with the remainder of the body, for receiving a pointed needle tip which is carried within the protector sheath. This provides an added, desired sequestering of the needle tip for improved safety. Alternatively, the retaining wall may be positioned at an acute angle, for example about 30° to 60° to the longitudinal axis of the body, which also defines a closed pocket with the remainder of the body for needle tip retention. If desired, the retaining wall may be essentially perpendicular to the longitudinal axis of the body (or in fact, it may be a partial front wall) to form a barrier wall against which the needle tip may impinge, for further protection against accidental needle sticks.

It also is desirable for the slots of the protector sheath body to curve toward the sheath bottom as they extend toward an open slot end at one end of the body. This has been found to facilitate the easy withdrawal of a needle emplaced in the venous system of a patient, with the needle tip directed in the direction of the one end of the body. As the needle is withdrawn, the needle protector can receive the needle wings in the slots. Because of the curve of the slots toward the bottom of the body, the needle wings are more easily received and engaged by the slots as the needle is withdrawn, with the needle protector sheath being held stationary, so that the needle may be withdrawn rearwardly into the needle protector sheath. The slots preferably extend through one end of the body at the slot end nearest the bottom aperture.

Thus, a needle protector sheath is provided which exhibits significant improvements in structure and functioning over those of the prior art.

The terms "top", "bottom", and "side" as used herein are generally exemplary in intent, and are not intended to exclude the use of a protector sheath of this invention in a different position of spatial orientation.

DESCRIPTION OF THE DRAWINGS

Referring to the drawings.

DESCRIPTION OF SPECIFIC EMBODIMENTS

Figure 3:
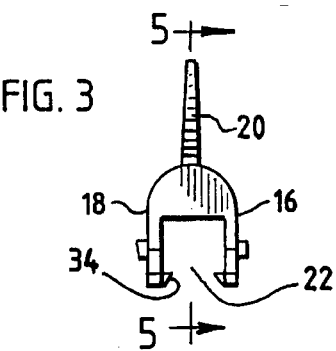
FIGS. 3 and 4 are, respectively, front and rear views of the sheath of FIG. 1, with the winged needle not being shown.
Figure 4:
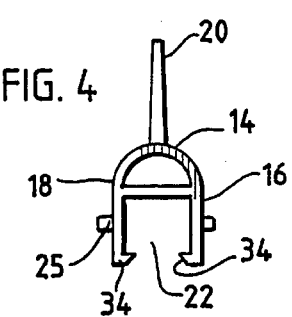
Figure 5:
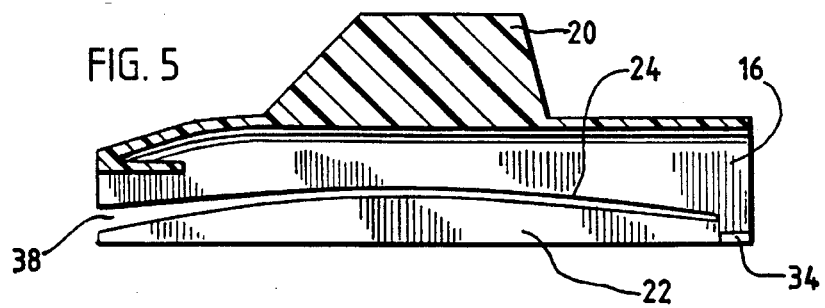
FIG. 5 is a longitudinal, sectional view of the sheath, with the "anchor" deleted.

Referring to FIGS. 1 through 8, a needle protector sheath 10 is disclosed, being generally similar in structure and function to the needle sheaths shown in U.S. Pat. No. 5,112,311 except as otherwise described herein. Sheath 10 comprises a body 12 which has a top wall 14 and side walls 16, 18, plus an optional gripping rib 20, integral with top wall 14, to facilitate manual gripping of the protector sheath. Apart from the presence of gripping rib 20, body 12 is shown by FIGS. 3 and 4 to be of generally U-shaped or C-shaped cross-section, defining an open bottom aperture 22 which extends from end to end of body 12.

Sheath 10 also defines a pair of slots 24, each slot 24 being defined in a separate side wall 16, 18, with each slot 24 extending through an end 23 of body 12. The purpose of slots 24 is to receive therethrough the wings 26 of a winged needle hub 28 projecting therethrough which, in conjunction with needle 31, is generally referred to herein as a "winged needle" 30. The winged needle 30 is shown to be connected to flexible tubing 32 of a fistula set used in hemodialysis, for example.

In the cited prior art patent, the needle protector sheath shown therein may be mounted upon tubing of a fistula set or the like from the needle or tube end of the set. To enclose completely the tube needle and/or hub with at least one end of the guard. It is then advanced distally to enclose the needle as the needle is being withdrawn from the patient. Specifically, the prior art protector sheath can be mounted on the winged needle of a set by passing the needle through the proximal end of the needle protector sheath, and then moving the sheath rearwardly out of the way of the needle, with the wings sliding into and along the slots of the protector sheath.

Figure 1:
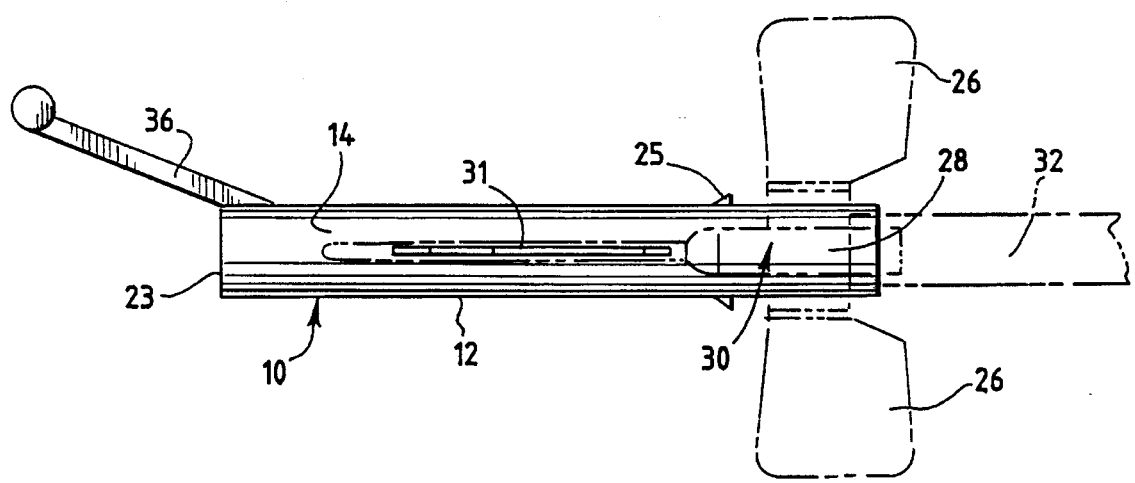
FIG. 1 is a plan view of one embodiment of the sheath of this invention, shown carrying a winged needle in retracted relation so that the sheath is surrounding the needle tip.
Figure 2:
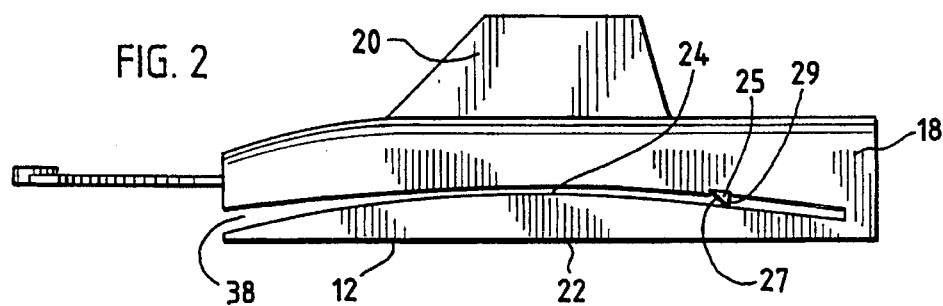
FIG. 2 is an elevational view of the sheath of FIG. 1.

Locking detents 25 are provided with a distally facing angled surface 27 and a proximally facing perpendicular surface 29, so as to provide snap fit retention for the wings sliding in slots 24 after the winged needle 30 has entered into fully enclosed relationship with protector sheath 10, as shown in FIG. 1, for the substantially permanent enclosing of the needle in the sheath.

As an advantage, the protector sheath of this invention is capable of being mounted on the tubing 32 of a fistula set from the side, even after the needle has been positioned in the vascular system of a patient, without the need for access to an end of the set. Instead, one can simply place the protector sheath laterally about tubing 32, with the tubing being retained to an extent by detents 34. Then, the protector sheath may slide forwardly relative to the needle as the needle is withdrawn, so that the needle becomes immediately enclosed by the protector sheath. This can be accomplished, as taught in the previously cited patent, by pressing a finger against projecting anchor 36, which may be an integral part of protector sheath 10, so that as the needle is withdrawn, the protector sheath is held in stationary position, causing the needle to retract into the sheath.

Figure 6:
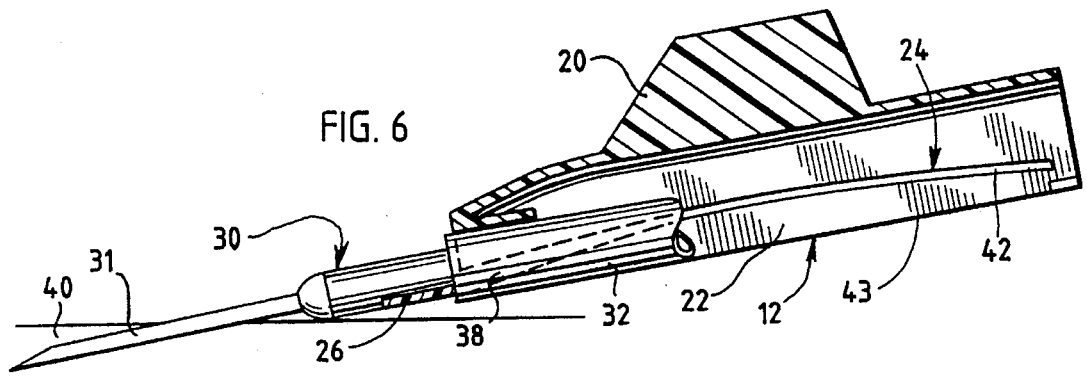
FIG. 6 is a longitudinal, sectional view of another sheath embodiment, showing the interrelationship of the sheath with a winged needle as the sheath is being advanced forwardly about the needle.
Figure 7:
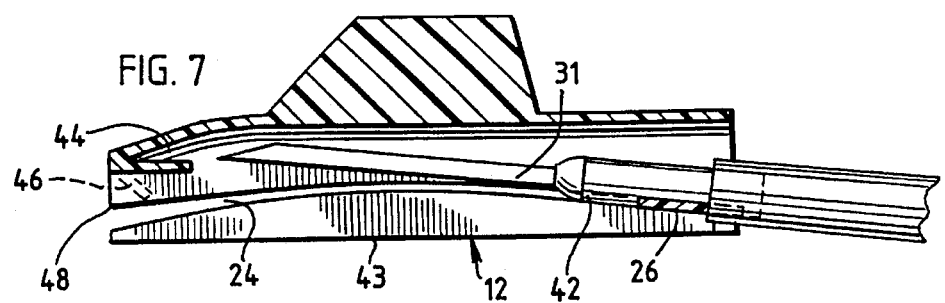
FIG. 7 is a longitudinal, sectional view showing the needle inside of the sheath of FIG. 6 in a position substantially corresponding to the position of FIG. 1.
Figure 8:
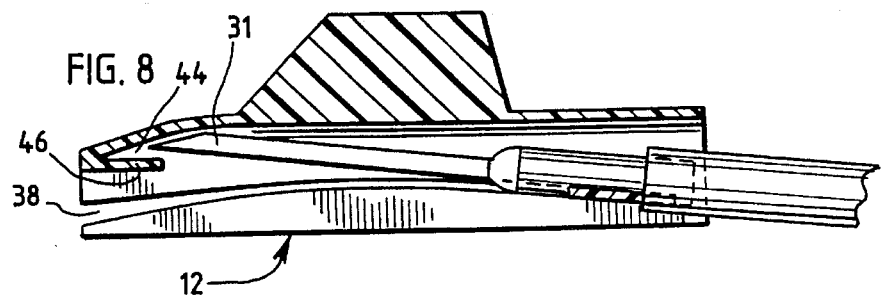
FIG. 8 is a longitudinal, sectional view of the sheath of FIG. 7, showing how the needle enclosed in the sheath can be advanced so that its point is inserted into an internal pocket of the sheath.

Because slots 24 may have a downward curve at their forward portions 38, it becomes easier for the forward open slot portions 38 to each engage a respective wing 26 as the winged needle 30 and body 12 are brought together, as implied by the different needle positions of FIGS. 6 and 7. Body 12 is of identical design to that of the previous embodiment except for the deletion of anchor 36. Thus, the proximity of the forward end 38 of each slit 24 to the lower edge of body 12 facilitates convenient engagement of the needle wings for withdrawal of the needle without excessive movement of needle 31 in the tissue 40 of the patient. Hence, the protector sheath of this invention can be applied to a needle which is being withdrawn with less patient discomfort. Also, forward slot ends 38 may be outwardly flared to more easily engage and receive the respective wings 26.

It can also be seen that slot 24 has a rear or proximal end 42 which also exhibits a slope toward the bottom edge 43 of body 12. The effect of this slope is to cause needle 31 to tilt upwardly as shown in FIG. 7. Then, body 12 can be retracted again relative to needle 31 to cause needle 31 to reside in the pocket 44 which is defined by needle tip retaining wall 46, as particularly shown in FIG. 8.

Needle tip retaining wall 46 is shown to be positioned substantially parallel to the longitudinal axis of body 12, to define a closed pocket 44 with the remainder of the body, for retention of the pointed tip of needle 31. Alternatively if desired, retaining wall 46 may extend at about a 45° angle to the axis of body 12, as shown in dotted lines in FIG. 7 to provide a more open pocket 44. Also if desired, retaining wall 46 may be substantially perpendicular to the axis of body 12, while being short enough to not completely obstruct the forward aperture 48 of body 12, to provide an obstructing wall for the needle point.

Figure 9:
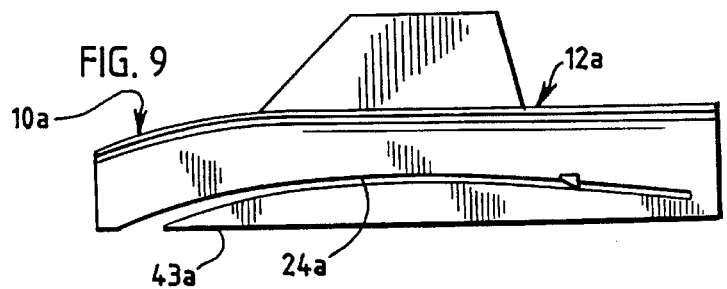
FIG. 9 is an elevational view of a modified version of the sheath of this invention.

Referring to FIG. 9, a protector sheath 10a is shown having a body 12a which may be of a design similar to that of the previous embodiments. In this particular embodiment, slots 24a on both sides of the side walls curve downwardly to pass through the lower edge 43a of body 12a, rather than passing through the end thereof as in the previous embodiments. Beyond that, the construction and use of protector sheath 10a can be similar or identical to the construction and use of the previous embodiments.

Figure 10:
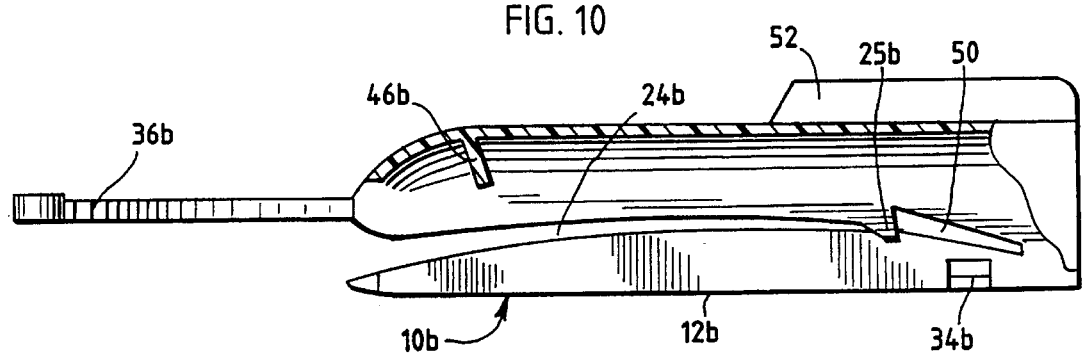
FIG. 10 a longitudinal, sectional view of another embodiment of the sheath of this invention.
Figure 11:
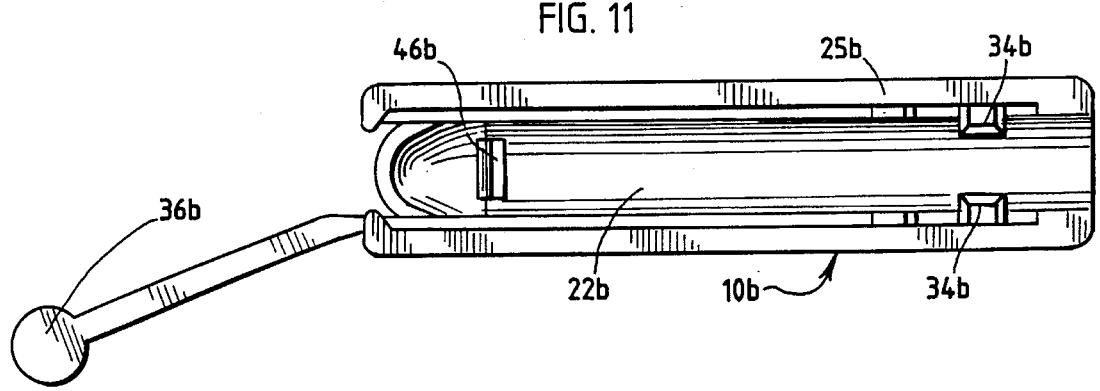
FIG. 11 is bottom, plan view of the sheath in FIG. 10.
Figure 12:
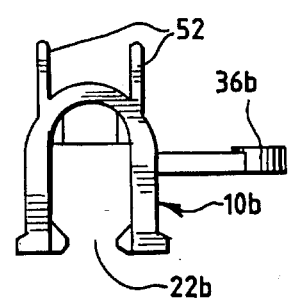
FIG. 12 is proximal end view of the sheath of FIG. 10.

Referring to FIGS. 10 through 12 another embodiment of the protector sheath 10b is shown, being similar in structure and function to the embodiment of FIGS. 1 through 8 except as otherwise disclosed herein.

Body 12b is of U-shaped configuration as shown in FIG. 12, defining open bottom aperture 22b as before. Slots 24b are defined in each sidewall, while anchor 36b is also provided as before.

In this embodiment, locking detents 25b are an integral part of the remainder of sheath 12b, but in this embodiment, the locking detents do not project outwardly to the side, but rather project into each slot 24b in such a manner that a retracting wing of a needle can cause deflection to pass through locking detents 25b to be permanently secured in proximal slot section 50 to lock the needle therein. It can be seen in this embodiment that needle tip retaining wall 46b does occupy an acute angle to the longitudinal axis in a manner previously discussed with respect to an earlier embodiment.

Detents 34b are used in a manner similar to the corresponding detents of the previous embodiments to releaseably retain the needle hub 30 or the tubing attached thereto within the U-shaped protector sheath.

Also, the needle protector sheath 10b carries a pair of spaced gripping flanges 52 instead of a single gripping member as in previous embodiments, the gripping flanges 52 being positioned adjacent the proximal end of the sheath. This better facilitates the gripping of the sheath, which is rather small. A single, central gripping member would have to be unduly large relative to the typically fairly small sheath of this invention. Gripping members 52 facilitate gripping of the sheath without the need for an oversized, single gripping member which would resemble a huge dorsal fin.

The above has been offered for illustrative purposes only, and is not intended to limit the scope of the invention of this application which is as defined in the claims below.

That which is claimed is:

1. A needle protector sheath which comprises a body having a top wall, sidewalls, and at least partially open ends;

a slot having an upper and a lower wall formed in each sidewall to slidingly receive a needle wing extending through each of said slots each slot extending through one of said ends; said protector sheath defining an open, bottom aperture extending the entire length of said body, to permit said sheath to be laterally applied to tubing connected to a winged needle, and to be advanced to a position where the needle point is recessed in said sheath and the needle wings extend through said slots.

2. The needle protector sheath of claim 1 in which said body further defines a needle tip retaining wall formed between said top and sidewalls adjacent one end of said body.

3. The needle protector sheath of claim 2 in which said retaining wall is positioned substantially parallel to the longitudinal axis of said body, to define a closed pocket with the remainder of said body, for retention of a pointed tip of a needle which is carried within said protector sheath.

4. The needle protector sheath of claim 1 in which said slots curve toward said bottom aperture as they extend toward one end of the body.

5. The needle protector of claim 4 in which said slots extend through said one end of said body at the slot end nearest the bottom aperture.

6. The needle protector sheath of claim 1 in which detents are provided on said sidewalls adjacent said bottom aperture, to help retain a winged needle within said body.

7. The needle protector sheath of claim 1 in which a retaining wall is positioned at an acute angle to the longitudinal axis of said body, to define a closed pocket with the remainder of said body, for retention of a pointed tip of a needle which is carried within said protector sheath.

8. The needle protector sheath of claim 1 in which at least one manual grasping member extends outwardly from said top wall.

9. A set for conveying blood to or from a patient which comprises flexible tubing and a winged needle carried at one end of the tubing, said set carrying the needle protector sheath of claim 1 in a position to permit forward sliding of the needle protector sheath to enclose the entire winged needle with wings of said winged needle projecting out of said sidewall slots.

10. A needle protector sheath which comprises a body having a top wall, sidewalls, and open ends; a slot having an upper and a lower wall formed in each sidewall to slidingly receive a needle wing extending through each of said slots, said protector sheath defining an open, bottom aperture extending the entire length of said body to permit said sheath to be laterally applied to tubing connected to a winged needle and to be advanced to a position where the needle point is recessed in said sheath and the needle wings extend through said slots, said slots sloping toward said bottom aperture as they extend toward one end of said body, and further in which said body defines a needle tip retaining wall formed between said top and sidewalls adjacent said one end of said body.

11. The needle protector sheath of claim 10 in which detents are provided on said side walls adjacent said bottom aperture, to help retain a winged needle within said body.

12. The needle protector of claim 11 in which said retaining wall is positioned substantially parallel to the longitudinal axis of said body, to define a closed pocket with the remainder of said body, for retention of a pointed tip of a needle which is carried within said protector sheath.

13. The needle protector of claim 12 in which said slots extend through one of said ends of said body at the slot end nearest the bottom aperture.

14. The needle protector of claim 13 in which an elongated anchor member extends forwardly from said needle protector sheath, to be manually pressed to retain said protector sheath as the needle is being withdrawn from the skin of a patient.

15. The needle protector sheath of claim 10 in which said slots are spaced from both ends of said body and curve to pass through the side of said needle protector sheath which defines said bottom aperture.

16. The needle protector sheath of claim 10 in which said retaining wall is positioned substantially parallel to the longitudinal axis of said body, to define a closed pocket with the remainder of said body for retention of a pointed tip of a needle which is carried within said protector sheath.

17. The needle protector sheath of claim 10 in which said retaining wall is positioned at an acute angle to the longitudinal axis of the body, to define a closed pocket with the remainder of said body, for retention of a pointed tip of a needle which is carried within said protector sheath.

18. The needle protector sheath of claim 10 in which at least one manual grasping member extends outwardly from said top wall.

19. The needle protector of claim 10 in which said slots extend through one of said ends of said body at the slot end nearest the bottom aperture.

20. A needle protector sheath which comprises a body having a top wall, sidewalls, and at least partially open ends, at least one slot having an upper and lower wall formed in at least one of said sidewalls to slidingly receive a needle wing extending through said slot, said protector sheath defining an open, bottom aperture extending the entire length of said body to permit said sheath to be laterally applied to tubing connecting to a winged needle and to be advanced to a position where the needle point is recessed in said sheath and said needle wing extends through said slot.

21. The needle protector tip of claim 20 in which said body further defines a needle tip retaining wall formed between said top and sidewalls adjacent one end of said body.

22. The needle protector sheath of claim 20 in which a plurality of said at least one slot comprises a plurality of slots that curve toward said bottom aperture as they extend toward one of said ends of the body.

* * * * *